United States Patent [19]

Schulz

[11] Patent Number: 5,707,857

[45] Date of Patent: Jan. 13, 1998

[54] PROCESS FOR THE REHABILITATION OF SOILS CONTAMINATED BY HYDROCARBONS AND OTHER BIODEGRADABLE SUBSTANCES

[75] Inventor: Christian Schulz, Gélos, France

[73] Assignee: Ceca S.A., Puteaux, France

[21] Appl. No.: 505,215

[22] PCT Filed: Jul. 21, 1994

[86] PCT No.: PCT/FR94/00913

§ 371 Date: Aug. 2, 1995

§ 102(e) Date: Aug. 2, 1995

[87] PCT Pub. No.: WO95/06715

PCT Pub. Date: Mar. 9, 1995

[30] Foreign Application Priority Data

Sep. 1, 1993 [FR] France ................... 93 10416

[51] Int. Cl.⁶ ................... B09B 3/00; C12S 1/00
[52] U.S. Cl. ................... 435/262.5
[58] Field of Search ................... 435/262.5

[56] References Cited

U.S. PATENT DOCUMENTS

| | | | |
|---|---|---|---|
| 3,883,397 | 5/1975 | Townsley | 195/100 |
| 3,959,127 | 5/1976 | Bartha | 210/11 |
| 4,401,762 | 8/1983 | Tellier | 435/243 |
| 4,460,692 | 7/1984 | Tellier | 435/243 |
| 5,340,376 | 8/1994 | Cunningham | 71/6 |
| 5,501,973 | 3/1996 | Mayfield | 435/262.5 |

FOREIGN PATENT DOCUMENTS

| | | | |
|---|---|---|---|
| 0507421 | 10/1992 | European Pat. Off. | 435/262.5 |
| 0 550 023 A2 | 12/1992 | European Pat. Off. | C12N 1/26 |
| 4031862 | 4/1992 | Germany | 435/262.5 |

*Primary Examiner*—Helen Pratt
*Attorney, Agent, or Firm*—Pennie & Edmonds

[57] ABSTRACT

The contaminated soil is first treated by spreading a nutrient for aerobic microbial flora of the N/P type in oleophilic form, then by the addition of straw and of a hydrophilic nutrient of the N/P/K type which are buried by mechanical mixing. A biological process takes place which brings the hydrocarbon content below 500 mg/kg of soil after some months. The oleophilic nutrient N/P is preferably a microemulsion of a solution of N/P salts in a fat-soluble hydrocarbon solvent.

10 Claims, No Drawings

PROCESS FOR THE REHABILITATION OF SOILS CONTAMINATED BY HYDROCARBONS AND OTHER BIODEGRADABLE SUBSTANCES

DESCRIPTION

This invention concerns the rehabilitation of polluted soils. It concerns particularly a method of treatment of industrial soils polluted by hydrocarbons and other biodegradable organic compounds.

The elimination of hydrocarbons contained in soils is essentially accomplished by the natural presence in the ground of aerobic bacteria which finds its only source of hydrocarbonic nourishment in those hydrocarbons. The biodegradation of the hydrocarbons is, therefore, a natural phenomenon, the speed of which depends on several factors, mainly on the concentration of the hydrocarbons and the characteristics of their hydrocarbonic chain, but also on other nutrients, which the microorganisms need for their vital functions.

In land areas in which carbon is found in excess due to pollution, bacteria consume, during aerobic fermentation phases, 15 to 30 times more carbon than nitrogen, depending on the biodegradability of the hydrocarbon (whether it is more or less biodegradable). The factors which limit biodegradation are then the nutrients in deficit, essentially nitrogen, then phosphorus among the middle elements and, to a lesser degree, sulphur and potassium. It is possible to limit this effect with respect to the elements in deficit so as to re-establish the optimal conditions for bacterial functioning if one fixes the weight ratios to be:

$C/N=20$ to 70

$N/P=2$ to 10

$C/P=75$ to 150

$C/S=100$ to 300

The nutritional complements necessary for the invention are those which are applied agriculturally with traditional chemical fertilizers. Also it has been advocated that complete fertilizers as commercially available or in similar formulations be used for biodecontamination and applied in a manner similar to conventional fertilization. Since the processes of degradation of hydrocarbons are noticeably longer than those which preside over vegetative assimilation in the realm of higher vegetation, preference has been given to formulations similar to slow fertilizers. The description of such an application can be found in the international application W091/19039 (Grace-Sierra Hort. Prod. Co.). Nevertheless, the efficacity of this process is limited because the pollution in question consists of hydrocarbon which generally is not uniformly distributed in the contaminated soil and because the distribution of the secondary nutrient which is added in hydrophilic form in a slow fertilizer does not completely establish conditions that are desirable for total biodegradation.

This invention remedies this disadvantage by introducing, in a rehabilitation process for a soil contaminated by hydrocarbons and other biodegradable products, a mixed treatment comprising the supply of a source of nutrients for micro-organisms under a double form, oleophilic and hydrophilic, along with an agent for aerating the soil.

The source of secondary nutrients for the micro-organisms in oleophilic form is derived from microemulsions of nourishing substances of N/P type in an aqueous solution in an external phase constituted by an organic fat-soluble solvent. These microemulsions are described in French Patent No. 80 20178, published under the number 2,490,672 (S.N.E.A. P) and its Certificate of Addition No. 81 16626, published under the number 2,512,057.

The source of secondary nutrients in hydrophilic form is a fertilizer programmatically distributed of the N/P/K type, or more simply of the N/P/O type, since the introduction of potassium is not generally necessary to the biodegradation conditions sought. In order to apply the invention more easily, according to principles which will be explained later, it is preferable to have at least two formulations, for example one 18/1/0 and one 15/7/0. The present fertilizers are formulated in slow-release form so as to avoid their being too rapidly washed away by precipitation. There is only the natural diffusion of the nutrients in order to assure the establishment of the ideal conditions of the local distribution of the secondary nutrients to the point in which the hydrocarbonic pollution has settled. It is advisable, therefore, to have a distribution as even as possible of grains of hydrophilic nutrients in the soil, which requirement requires that their grains be thinner than those of ordinary fertilizers. Thus while conventional fertilizers contain 30 granules per gram, the hydrophilic nutrients of the present invention have from 100 to 200 granules per gram. Moreover, they will be vividly colored in order to make their distribution visible in the course of their being spread over and incorporated into the soil being treated.

The aeration agent of the soil facilitates a process of decontamination through aerobic bacteria. For this, one uses wood chips or sawdust, corn cobs, or straw. Straw, especially straw of gramineous cereals, is particularly interesting because it is a hydrophobic material, its property being used in the structure of thatch roofs. It has been noted that when straw has been mixed with a soil contaminated by hydrocarbons, it would stabilize a part of the hydrocarbons which would thus find themselves placed in conditions favorable to their aerobic biodegradation, namely the hollow tubes of straw. This mechanism is probably improved in the presence of surfactants brought in by the microemulsion used as nutrients in a hydrophobic form. The speed and the final result of the process of decontamination are considerably improved.

For the operation of the process, the first thing to be done is to confirm the presence of an adequate bacterial flora (Pseudomonas Cichorii, Rhodococcus Fascians, Athrobactus divers, etc.). This confirmation is realized through a bacterial test consisting of bacterial numeration through culture in a solid aerobic medium in a Petri dish. One follows with a dosage of soil in carbon, nitrogen, and phosphorus, and with an analysis, at least a brief one, of hydrocarbons present as aliphatics, of which the duration of the degradation on the order of 6 months is relatively fast, and as aromatics, of which the duration of degradation is clearly longer (8 to 12 months for the aromatics, 16 months for the polycyclics). Given this data, one determines the dosages of oleophilic and hydrophilic bacterial nutrients so as to lead the overall content of soil treated with C/N/P to optimal values of approximately 100/20/1. As a starting point, an oleophilic/hydrophilic nutrient distribution of 10/90 is used. The more aromatics and/or polycyclics the hydrocarbons contain, the more this ratio is raised.

For the treatment of the terrain, one begins by spreading manure or by a powdered oleophilic nutrient, used preferably in concentrated form. When the hydrocarbon contamination is intense, the site is left alone until the initial black color of the soil becomes brown or yellow-brown. Usually this change requires two to seven days. Then one returns to the site and scatters straw on the soil in a dosage of 0.1% to 5%, depending on the physical characteristics of the soil, and a granular hydrophilic nutrient in the determined dosage. Then follows intense mixing with the assistance of any convenient machine, whether agricultural or industrial. With moderately contaminated soils, the spreading of the oleophilic nutrient and of the straw associated with the hydrophilic nutrient is accomplished simultaneously. One may leave the soil fallow, or excavate it and stockpile it in swaths, depending on how the treated areas must be used. The biological process develops over variable periods of time, generally from 6 to 18 months according to the intensity of the pollution and the nature of the polluting hydrocarbons. One follows the progression of the biodecontamination by regular sampling and measuring the hydrocarbons. The grounds are considered decontaminated when their hydrocarbon content is brought to levels inferior to 500 mg/kg, measured according to the standard AFNOR NFT 90114 (level on the date of the patent application, modifiable to comply to current regulations).

EXAMPLE 1

A zone demarcated within an enclosed area of an abandoned industrial site was contaminated by motor greases and draining oils. The average dosage of hydrocarbons was 62 grams per kilogram of soil. The test for the presence of aerobic bacteria came out positive, with a total aerobic flora content of $4 \times 10^7$ bacteria per gram of soil. The following conditions of treatment were determined and applied:

oleophilic nutrient, a product available from CECA S.A. under the name of INIPOL® EAP22, which is a microemulsion of N/P 10/1 having a density of about 0.996, at the rate of 100 g/m$^2$;

straw, to be spread at the rate of 1% by volume;

hydrophilic nutrient, a composition N/P/K 15/7/0, available from CECA S.A. under the name of INIPOL® SP2, in dark green balls (200 granule/grams) protected by an anti-diffusion layer, to be incorporated at the rate of 1000 g/m$^2$.

The oleophilic nutrient was spread with a pulverizer on the surface of the soil and the site was left fallow for eight days. Then one spread the straw manually (1% in volume) and the grains of hydrophile nutriment. Mixing of the earth was carried out with a mechanical shovel in three successive runs until a homogeneous mixture was obtained. The material was then excavated and placed in swaths about 5 meters wide and 25 meters long on an elevation of 1.5 meters, arranged in an area protected by a geo-membrane. The change in the hydrocarbon content was determined (Table 1).

TABLE 1

Total Hydrocarbons (ppm) as a Function of Time

| Duration | Initial | 2 months | 4 months | 6 months | 8 months |
|---|---|---|---|---|---|
| Zone 1 | 62028 | 27765 | 5031 | 939 | 114 |

Eight months later, the then-decontaminated earth was left on the site in order to create an open space.

EXAMPLE 2

The soil treated soil was the object of severe contamination by paint solvents. After a first intervention on the site with an oleophilic cylinder (see the French patent published under the number 2,528,412) in order to eliminate the hydrocarbons loose on the surface, the average content of total hydrocarbons in the soil to be treated was 965 mg/kg, of which 57 mg/kg was toluene. The bacterial test detected the presence of aerobic bacteria adapted to the biodegradation of light aromatics ($3 \times 10^8$ bacteria per gram of soil).

The conditions of the treatment were established as follows:

pulverization of the oleophilic nutrient Inipol® EAP22 in a dose of 100 g/m$^2$;

addition of a hydrophilic nutrient of the composition N/P/K 18/1/10, available from CECA S.A. under the name of Inipol® SP1, in a dose of 500 g/m$^3$;

three runs of mixture with soil.

The treated material was excavated and placed in 10 swaths 5 meters wide, 50 meters long, and 1.5 meters high, placed on a waterproof zone. Some perforated drains were installed in the heart of the swaths to complete the ventilation of the material. The change was as follows:

| Duration | Initial | 1 month | 3 months | 6 months |
|---|---|---|---|---|
| Total HC (ppm) | 965 | 895 | 382 | 48 |
| Toluene (ppma | 57 | <Beginning | <Beginning | <Beginning |

After 6 months, the soil considered contaminated was used again and spread out on the site.

The process may be applied to earth where the presence of bacteria is suited to the biodegradation of the hydrocarbon discussed. The process according to the invention is equally applicable to sterile contaminated soils which are first treated by bacterial inoculation/insemination.

The method of soil rehabilitation is also applicable to contaminations by chemical compounds, for example paints or other biodegradable organic compounds.

I claim:

1. Process for the rehabilitation of soils polluted by hydrocarbons in which the activity of an endogenous microbial flora suited to the degradation of hydrocarbons is fostered through the addition of nutrients that are scarce in relation to an ideal ratio for bacterial development of 100/20/1, characterized in that one applies to the soil to be treated:

a nutrient of the nitrogen/phosphorous type, in the oleophilic form of a microemulsion of solution of nitrogen/phosphorous salts in a fat-soluble hydrocarbon solvent, a nutrient of the nitrogen/phosphorous/potassium type, in the hydrophilic form of granules of nitrogen/phosphorous/potassium salts, and a texturing agent for aeration.

2. Process according to claim 1, characterized in that the hydrophilic nutrient N/P/K is in the form of granules of N/P/K salts surrounded by an anti-diffusion barrier.

3. Process according to claim 2, characterized in that the granules are of such size as to provide 100 to 200 granules per gram.

4. Process according to claim 3, characterized in that the granules are vividly colored.

5. Process according to claim 1, characterized in that the texturing agent for aeration is straw.

6. Process according to claim 1, characterized in that one carries out:

(a) a spraying of the oleophilic nutrient on the surface of the soil to be treated, then (b) a spreading of the texturing agent and of the hydrophilic nutrient, then (c) a mixing of the treated soil to obtain an intimate mixture of all of its components.

7. Process according to claim 6, characterized in that phase (b) of the operation is deferred from 2 to 7 days.

8. Process according to one or the other of claims 6 or 7, characterized in that the soil to be treated is retained on-site until the hydrocarbon content is lowered to the desired level of concentration.

9. Process according to one or the other of claims 6 or 7, characterized in that the treated soil is excavated and left in swaths until the hydrocarbon content is lowered to the desired level of concentration.

10. Process for the rehabilitation of soils polluted by hydrocarbons in which the activity of an endogenous microbial flora suited to the degradation of hydrocarbons is fostered through the addition of nutrients that are scarce in relation to an ideal ratio for bacterial development carbon/nitrogen/phosphorous of 100/20/1, characterized in that one applies to the soil to be treated:

- a nutrient of the nitrogen/phosphorous type in oleophilic form, wherein said nutrient is a microemulsion of the type: solution of nitrogen/phosphorous salts in a fat-soluble hydrocarbon solvent and
- a nutrient of the nitrogen/phosphorous/potassium type in hydrophilic form.

* * * * *